US005212086A

United States Patent [19]

Watson et al.

[11] Patent Number: 5,212,086

[45] Date of Patent: May 18, 1993

[54] FUNGAL HERBICIDES

[75] Inventors: Alan K. Watson, Pincourt; Richard D. Reeleder, Montreal, both of Canada; Juan Ormeno-Nunez, Santiago, Chile

[73] Assignee: The Royal Institution for the Advancement of Learning (on Behalf of McGill University), Ste. Anne De Bellevue, Canada

[21] Appl. No.: 707,924

[22] Filed: May 28, 1991

Related U.S. Application Data

[63] Continuation of Ser. No. 614,699, Nov. 19, 1990, abandoned, which is a continuation of Ser. No. 145,285, Jan. 19, 1988, abandoned.

[30] Foreign Application Priority Data

Feb. 3, 1987 [CA] Canada .................................. 528909

[51] Int. Cl.[5] .......................... C12N 1/14; A01N 1/02

[52] U.S. Cl. ................................ 435/252.1; 435/254; 504/117

[58] Field of Search .................. 435/252.1, 254; 71/79

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,390,360 | 6/1983 | Walker | 71/79 |
| 4,419,120 | 12/1983 | Walker | 71/79 |
| 4,605,668 | 8/1986 | Takahashi et al. | 71/3 |
| 4,715,881 | 12/1987 | Andersen et al. | 71/65 |
| 4,753,670 | 6/1988 | Leth | 71/79 |

FOREIGN PATENT DOCUMENTS 0136850 4/1985 European Pat. Off. .

OTHER PUBLICATIONS

Bugaret et al., "Elemental Sulfur and Control of Dead-Arm . . . ," CA 103, 33401 e, 1985.

Gautam et al., "Changes in Vitamin C content of Citrus . . . ," CA 103, 85249 f, 1985.

Tekrony et al., "Effect of Benomyl Applications on Soybean . . . ," CA 103, 173879 s, 1985.

Fernald, M. L., ÷Gray's Manual of Botany, pp. 1180–1181, D. Van Nostrand Co., 1970.

Rosenthal, S. S., et al., Biological Abstracts, vol. 75, abstract no. 61773 (1983).

*Primary Examiner*—Robinson, Douglas W.
*Assistant Examiner*—Deborah K. Ware
*Attorney, Agent, or Firm*—Cushman, Darby & Cushman

[57] ABSTRACT

A method for the biological control of field bindweed using a fungus *Phomopsis convolvulus* Ormeno. This fungus is a newly described pathogen, which produces foliar lesions in the field bindweed, and is the first fungal pathogen that can control field bindweed present among agricultural crops.

1 Claim, No Drawings

FUNGAL HERBICIDES

This is a continuation of application Ser. No. 07/614,699, filed on Nov. 19, 1990, which was abandoned upon the filing hereof, which was a continuation of Ser. No. 07/145,285 filed Jan. 19, 1988 which is now abandoned.

This invention relates to a method for the biological control of weeds and, more particularly, to such a method using a fungal pathogen.

Field bindweed (*Convolvulus arvensis* L.) is a prostrate or climbing herbaceous perennial that is a major problem weed in agricultural areas throughout the temperate regions of Europe, South America, Southern Africa, Western and Southeastern Asia, Australia and the Pacific Islands. It is widely distributed in North America and has been reported in forty-five states of the United States of America and in all Canadian provinces except Newfoundland and Prince Edward Island. It is ranked as the twelfth most important weed in the world.

Field bindweed reduces crop yields and its twining growth habit interferes with harvesting operations. It is a trailing, climbing perennial vine which twists, in an anti-clockwise direction, around stems of other plants or itself. The alternate, glabrous leaves are oblong, sagittate or ovate, up to 5 cm long, with short petioles. Flowers are usually solitary, axillary, pink or white, with funnelform corolla up to 3.5 cm long and 2 cm diameter. Abundant seeds are produced in two-valved capsules, each containing 1–4 ovoid- to pear-shaped seeds. These seeds can remain dormant in the soil for up to 50 years. Established plants of field bindweed have extensive, well-established root systems with a central, robust tap root down to 7 m deep, and extensive, cord-like lateral roots. The numerous vegetative rootbuds on the root system are the major reasons for spread and perennation of field bindweed.

Field bindweed is extremely persistent and difficult to control, although some degree of control can be obtained through repeated cultivation. However, this method is extremely laborious, expensive and not applicable to most cropping systems. Chemical herbicides such as 2,4-dichlorophenoxyacetic acid can be used for selective control of field bindweed in grass crops while glyphosate [(N-phosphonomethyl) glycine] can be used for non-selective control of field bindweed. It is well recognized, however, that there are problems associated with chemical herbicides which problems include damage to desirable crop plants, drift onto neighbouring susceptible crops and toxicity to non-target organisms.

Although the merits for using plant pathogens to control weeds in annual crops have been discussed previously for Colletotrichum species (U.S. Pat. Nos. 3,849,104 and 3,999,973), Fusarium species (U.S. Pat. No. 4,419,120) and Alternaria species (U.S. Pat. No. 4,390,360), no plant pathogens have been used to date to control the major problems of field bindweed.

Thus, it is an object of the present invention to provide a biological method to control field bindweed in agricultural crops.

It is a further object to provide a plant growth regulating composition of a fungal microorganism of use in the control of field bindweed.

It is yet a further object to provide a biologically pure culture of a fungal microorganism of use in the control of field bindweed.

Accordingly, the invention provides a method of controlling field bindweed plants in agricultural crops which method comprises applying to the plants or to the locus of the plants an effective amount of the fungus *Phomopsis convolvulus* to infect and produce typical lesions in said plants so as to inhibit the growth of or kill said plants.

The method according to the invention has been found to control field bindweed without causing harm to agricultural crops. The fungus *Phomopsis convolvulus* Ormeno infects the field bindweed to cause leaf spots and anthracnose foliar lesions which have a growth inhibiting effect on the plant and which may kill the plant.

The fungus *Phomopsis convolvulus* Ormeno of use in the practice of the invention is a novel pathogen and the first fungal pathogen known to control field bindweed. It is on deposit with the Department of Plant Science, Macdonald College of McGill University in Ste-Anne-de-Bellevue, Quebec; the Biosystematics Research Institute, Agriculture Canada in Ottawa, Ontario, and assigned the following accession number DAOM 196873; the Commonwealth Mycological Institute in Kew, England, and assigned the following accession number IMI 312959.

Thus, in a preferred feature the invention provides a method as hereinbefore defined wherein the fungus is *Phomopsis convolvulus* IMI 312959.

The fungus may be formulated with a suitable agriculturally acceptable carrier and applied as a foliar spray, wettable powder or in granular form.

Thus, in a further feature the invention provides a plant growth regulating composition comprising a plant growth regulating effective amount of a culture of microorganisms of the species *Phomopsis convolvulus* in association with an agriculturally acceptable carrier.

The fungus *Phomopsis convolvulus* Ormeno of use in the practice of the invention is, as hereinbefore described, a novel pathogen and is the first fungal pathogen that has been described to control field bindweed.

Accordingly, in a further feature the invention provides a biologically pure culture of the fungal microorganism having the identifying characteristics of *Phomopsis convolvulus.*

*Phomopsis convolvulus* IMI 312959 may be provided in specific forms such as freeze dried, in composition with a solid or liquid diluent or as a culture in a culture medium e.g. containing a source of assimilable carbon, a source of nitrogen and, if desired, vitamins and inorganic salts and/or substantially free from other micro-organisms.

The method according to the invention consists of broadcasting a field with the fungus *Phomopsis convolvulus* to effect which control of the field bindweed while not harming crop plants. The exact method of contacting *Phomopsis convolvulus* with the bindweed may be chosen for convenience. Clearly, the contact must be of a proper manner and duration for infection to occur. We have found it necessary that a sufficient moisture content in the medium surrounding the fungal spores be maintained for at least twelve hours in order to effect germination of the spores and subsequent infection of the plant.

Preemergence or postemergence applications of granules can be used. The granular formulation of a foliar pathogen for soil application for preemergence weed control is difficult to recognize because soil-inhabiting organisms compete with the pathogen. The satisfactory performance of this fungus for preemergence weed control is determined by the method of formulation.

Preferably, the fungus is applied as a foliar spray.

The microorganism may be cultured according to the method as hereinafter described. Because of the high level of activity of the culture and for greater ease of handling, storage and application, it is preferable to formulate the culture into compositions which include inert carriers or diluents, and, preferably, surface active agents and, optionally, other ingredients to assist the product to adhere to plant surfaces, improve rainfastness, or to resist degradation by, for example, sunlight. Such compositions may be applied by conventional application techniques, for example, by spraying the plants or by treating the soil in which the plants are growing or are to be planted.

The invention thus also provides compositions for use in the method of this invention in which the culture is incorporated in a liquid, or paste or jelly-like medium, or is admixed with an inert solid granular or particulate carrier. For application, for example, to the foliage of plants, formulations in the form of wettable powders and aqueous suspensions designed to be diluted with water before spraying are particularly preferred. The compositions may also incorporate emulsifying agents, suspending agents, and also where viable cultures are used, nutrients to sustain the viability of the microorganisms.

Colonies of *Phomopsis convolvulus* Ormeno have the following morphological characteristics.

The colonies of *Phomopsis convolvulus* in potato dextrose agar floccose, are dense with abundant white mycelium, reverse side of cultures colorless, with small, individual, pulvinate superficial stromata. Conidiomata pycnidial, solitary, immersed becoming erumpent, globose to subglobose, depressed, uni- or multi-loculated, textura angularis, up to 300 μm diameter, uni- or multi-ostiolated, ostioles pupillate, up to 50 μm wide; pycnidial wall composed of many layers of light brown, laterally compressed cells, sclerotized and heavily pigmented around the ostiolar region. Conidiogenous cells, hyaline, simple, phialidic, up to 5 μm long, arising directly from the intermost layer of cells lining the pycnidial cavity or from 1-septate conidiophores. Alpha-conidia hyaline, oblong to fusiform-ellipsoid, mostly with two large guttules located at both extremes, rarely 3-guttulate, sometimes slightly constricted in the middle; length (10)11-12(15) μm; width 3-4(5) μm; length/width ratio mostly 2.5-3.0. Beta-conidia filiform, hyaline, blunt at one end, tapered at the other, often hamate at the tapered end, rarely straight; found only in culture; length 17-33 μm; width 0.5-1.5 μm.

The *Phomopsis convolvulus* IMI 312959 used in the following studies was isolated from leaf lesions from diseased field bindweed plants collected in the vicinity of Ste-Anne-de-Bellevue, Quebec. Small sections (1 $cm^2$) of diseased leaf tissue were dissected and surface sterilized for 5 min. in 1% (v/v) sodium hypochlorite solution, rinsed in sterile water, placed on sterile paper for 5 min. to dry, and then placed in petri dishes containing malt extract agar (MEA) acidified to pH 4.8 with 88% lactic acid. Cultures were incubated at 21° C. on the laboratory bench with no supplemental lighting. Advancing edges of the original cultures were transferred to "V-8" (Trade Mark) juice agar and stored at 4° C. in the dark.

Actively sporulating cultures of *Phomopsis convolvulus* were grown on acidified potato dextrose agar (PDA) and flushed with sterile distilled water. The resulting spore suspension was transferred to petri dishes containing PDA 1.2 [12 g/L potato dextrose broth, 15 g/L bacto agar, 100 mg/L novobiocin and 100 mL/L bindweed decoction (200 g fresh bindweed leaves/L water, boiled for 30-40 min., filtered, autoclaved for 15 min.)] These PDA 1.2 cultures were incubated for 2-3 weeks on the laboratory bench at 21° C. without supplemental lighting. Plates were flooded with 10 mL of water and yielded $0.9-1.2\times10^{10}$ spores/mL.

The general method of treating field bindweed plants with cultures of *Phomopsis convolvulus* IMI 312959 was as follows.

All plants were sprayed to wetness (noticeable coalescing of droplets on the plant surface) with alpha-conidia suspensions of *Phomopsis convolvulus* generally containing $4-6\times10^6$ spores/mL and 0.1% gelatin (wt/v). After spraying, inoculated plants were air dried for 10 min., placed into a dew chamber at 20° C. in the dark for 24 hours, and then placed in growth chambers at 20° C. night/25° C. day with 15-hour photoperiod of 300 $\mu\epsilon/sec/m^2$ light intensity. Seedlings or shoots of test plants were inoculated at the 2-4 leaf stage unless otherwise indicated. Control plants were sprayed with 0.1% gelatin solution only.

EXAMPLE I

This Example illustrates inoculum production for the purpose of obtaining sufficient *Phomopsis convolvulus* IMI 312959 spores to effect field bindweed plants.

*Phomopsis convolvulus* was grown on acidified potato dextrose agar (aPDA) or acidified "V-8" agar for 30-40 days on the laboratory bench at 21° C. with one week of supplemental lighting with near ultraviolet light. Ten mL of sterile distilled water were deposited onto these actively sporulating plate cultures with the aid of a syringe. The conidial matrix droplets mixed rapidly with the water as the plate surface was flushed several times. The resulting conidial suspension was transferred to petri dishes containing PDA 1.2 [12 g/L potato dextrose broth, 15 g/L bacto agar, 100 mg/L novobiocine and 100 mL/L bindweed decoction (200 g fresh bindweed leaves/L water, boiled for 30-40 min., filtered and autoclaved)]. Discrete droplets of the conidial suspension were aseptically deposited on the agar surface with 0.4-0.5 mL of the conidial suspension used per dish (9 cm diam.). These dishes were incubated at 21° C. in light or dark for 2-3 weeks. Each dish was flooded with 10 mL water and yielded $0.9-1.2\times10^{10}$ spores/mL. In petri dishes sealed with parafilm conidial viability was retained, with greater than 95% germination, after 3 months of storage under ambient laboratory conditions. Conidial suspensions remained viable for nine months in 10% sucrose solution stored at −70° C.

EXAMPLE II

This Example illustrates the effect of inoculum concentration on disease development.

Fresh conidial of *Phomopsis convolvulus* IMI 312959 were suspended in a 0.1% gelatin solution and adjusted to concentrations of $1\times10^5$, $5\times10^5$, $1\times10^6$, $5\times10^6$ and $1\times10^7$ spores/mL. Five pots, each containing three seedlings in the 3-5 leaf stage, were inoculated with each conidial concentration. Control seedlings were sprayed with a 0.1% gelatin solution. Inoculated plants were placed in a dew chamber at 20° C. for 24 hours, then placed in growth chambers at 20° C. night/25° C. day with 15-hour photoperiod of 300 $\mu\epsilon/sec/m^2$. After 15 days foliar necrosis was visually assessed, and % mortality and dry weight were determined. The experiment was repeated once. The results presented in TABLE I show that damage and death of the field bindweed plants was dose dependent. Further that spore concentrations above $1.0\times10^6$ gave excellent control of field bindweed. Damage and death of field bindweed inoculated with *Phomopsis convolvulus* IMI 312959 was dose dependent (TABLE I). Spore concentrations above $1.0\times10^6$ provided excellent control of field bindweed.

TABLE 1

Effect of the inoculum concentration (spores/mL) on disease expression in field bindweed plants inoculated with *Phomopsis convolvulus* IMI 312959.

| INOCOLUM (Spores/mL) | DISEASE RATING[1] | MORTALITY (%) | DRY MATTER (g/pot) |
|---|---|---|---|
| $1.0\times10^5$ | 0.9 a[2] | 0 | 0.47 d[3] |
| $5.0\times10^5$ | 2.0 ab | 0 | 0.33 c |
| $1.0\times10^6$ | 3.9 b | 66.7 | 0.17 b |
| $5.0\times10^6$ | 4.0 b | 100.0 | 0.13 a |
| $1.0\times10^7$ | 4.0 b | 100.0 | 0.11 a |

[1]Ratings: 0 = no visible symptons; 1 = <25% necrosis; 2 = 25%-50% necrosis; 3 = 51%-75% necrosis; 4 = >75% necrosis
[2]Means followed by the same letter in the column are not significantly different at P = 0.05, according to the Friedman test.
[3]Means followed by the same letter in the column are not significantly different at P = 0.05, according to Tukey's W Test.

EXAMPLE III

This Example illustrates the effect of the dew period on disease development in field bindweed.

Bindweed seedlings at the 3-5 leaf stage were inoculated with a conidial suspension of $5\times10^6$ spores/mL in a 0.1% gelatin solution. Control plants were sprayed with a 0.1% gelatin solution. Inoculated plants were subjected to dew periods of 0, 1.5, 3, 6, 12, 24 and 48 hour at 20° C. Each treatment consisted of three seedlings/pot and each treatment was replicated five times. Immediately after each dew period, plants were transferred to growth cabinets at 20° C. night/25° C. days with 15-hour photoperiod of 300 $\mu\epsilon/sec/m^2$ light intensity. Disease rating, mortality and dry weight were assessed after 15 days. The results are presented in TABLE 2. Limited disease development occurred on field bindweed seedlings subjected to a dew period of less than 3 hours. Dew period of 12 hours caused extensive damage to field bindweed, but some plants were able to regrow. Dew periods of 24 hours and more resulted in 100% mortality.

TABLE 2

Effect of the number of dew hours required on disease expression of *Phomopsis convolvulus* in field bindweed.

| DEW HOURS | DISEASE RATING[1] | MORTALITY (%) | DRY MATTER (g/pot) |
|---|---|---|---|
| Control | 0 a[2] | 0 | 1.02 c[3] |
| 0 | 0 a | 0 | 0.85 c |
| 1.5 | 0 a | 0 | 1.00 c |
| 3.0 | 1.3 a | 0 | 0.98 c |
| 6.0 | 2.8 ab | 8.3 | 0.56 b |
| 12.0 | 4.0 b | 66.7 | 0.15 a |
| 24.0 | 4.0 b | 100.0 | 0.12 a |
| 48.0 | 4.0 b | 100.0 | 0.12 a |

[1]Ratings: 0 = no visible symptons; 1 = <25% necrosis; 2 = 25%-50% necrosis; 3 = 51%-75% necrosis; 4 = >75% necrosis.
[2]Means followed by the same letter in the column are not significantly different at P = 0.05, according to the Friedman Test.
[3]Means followed by the same letter in the column are not significantly different at P = 0.05 according to Tukey's W Test.

EXAMPLE IV

This Example illustrates the effect of plant age on Disease Development and Regrowth.

Field bindweed seedlings at the 3-4 leaf stage, seedlings at the 5-7 leaf stage, shoots (2-4 leaf stage) grown from 3-4 cm root pieces, and shoots (2-4 leaf stage) regrowth from established (2-month old) root stocks were inoculated with a conidial suspension of $4\times10^6$ spores/mL in a 0.1% gelatin solution. Control plants were treated with a 0.1% gelatin solution. Each treatment was replicated five times. After inoculation, plants were given a dew period of 24 hours at 20° C. and placed in a growth chamber at 20° C. night/25° C. day with 15-hour photoperiod of 300 $\mu\epsilon/sec/m^2$ light intensity. Plant mortality was assessed after 2 weeks and all plants were then re-inoculated at the same rates and under the same conditions. Plant mortality was again assessed after 2 weeks. The results are shown in TABLE 3. Only a single inoculation was required to kill young field bindweed seedlings. Complete foliar necrosis was obtained on all aged plant material, but regrowth occurred in established plants. A second inoculation resulted in high to complete mortality of all aged plant material.

TABLE 3

Effect of the number of inoculations and age of the bindweed plants on the disease development of *Phomopsis convolvulus.*

| PLANT GROWTH STAGE | PLANT MORTALITY (%) FIRST INOCULATION | SECOND INOCULATION |
|---|---|---|
| SEEDLINGS | | |
| 3-4 leaves | 100 | 100 |
| 5-7 leaves | 71 | 100 |
| SHOOTS | | |
| 3-4 leaves (root sections) | 100 | 100 |
| 3-4 leaves (established plant) | 0 | 40 |

EXAMPLE V

This Example illustrates the host range of *Phomopsis convolvulus.*

A total of 114 plant species from 60 genera and 16 families were tested to determine their reaction to *Phomopsis convolvulus.* All plants were derived from seeds except *Calystegia soldanella* (rhizomes), *Ipomoea batatas* (rooted vine cuttings) and *Vitis vinifera* (rooted canes). A total of 12 plants (3 plants/pot replicated 4 times) of each test species were inoculated to wetness with a conidial suspension of $5-6\times10^6$ spores/mL in a 0.1% gelatin solution. Another 12 plants of each species were sprayed with 0.1% gelatin. At each spraying, bindweed plants were also inoculated to ensure virulent inoculum. Inoculated plants were placed in a dew chamber at 20°

C. for 24 hours, then transferred to growth chambers at 20° C. night/25° C. day with a 15-hour photoperiod with 300 $\mu\epsilon/sec/m^2$ light intensity. The results are shown in TABLE 4. The only plant species actually killed by *Phomopsis convolvulus* was field bindweed. However, disease developed on all the Convolvulus and Calystegia species tested. We have found that *Phomopsis convolvulus* is highly virulent on Convolvulus and Calystegia species, is a weak pathogen on table beet, safflower and *Quamoclit pennatta*, and not a pathogen of the other plants tested.

TABLE 4

Response of various plant species to *Phomopsis convolvulus* under controlled environment conditions.

| SPECIES TESTED | DISEASE REACTION[1] |
|---|---|
| Family CONVOLVULACEAE | |
| *Convolvulus arvensis* L. | S |
| *Convolvulus unicaulis* L. "Blueflash" | S |
| *Convolvulus tricolor* L. "Royal Ensign", "Cambridge blue", "Dwarf mixed" | S |
| *Convolvulus althaeoides* L. | S |
| *Convolvulus cneorum* L. | S |
| *Convolvulus sp.* "Mixed", "Dwarf variegated", "Imperial Jap." | S |
| *Calystegia atripicifolia* (H.) Hall. | S |
| *Calystegia collina* (H.) Brum. | S |
| *Calystegia fulcrata* Gray | S |
| *Calystegia longipes* (Wat.) Brum. | S |
| *Calystegia macrostegia* (Gree.) Brum. | S |
| *Calystegia malacophylla* (Gree.) Munz | S |
| *Calystegia occidentalis* (Gray) Brum. | S |
| *Calystegia purpurata* (Gree.) Brum. | S |
| *Calystegia sepium* (L.) R. Br. | S |
| *Calystegia silvatica* (Kit.) Griseb | S |
| *Calystegia soldanella* (L.) R. Br. | S |
| *Calystegia stebbinsii* Brum. | S |
| *Calystegia subacaulis* Hook & Arn. | S |
| *Ipomoea alba* L. | R+ |
| *Ipomoea batatas* (L.) Lamb. "Travis" | R+ |
| *Ipomoea hederacea* Jacq. | R+ |
| *Ipomoea hederifolia* L. | R+ |
| *Ipomoea nil* (L.) Roth. "Scarlet O'Hara" | R |
| *Ipomoea purpurea* Lam. | R |
| *Ipomoea quamoclit* L. | R |
| *Ipomoea trichocarpa* Elliot | R+ |
| *Ipomoea tricolor* Cav. "Blue star", "Pearly Gates" | R+ |
| *Ipomoea violacea* Hook | R+ |
| *Ipomoea wrightii* Gray | R+ |
| *Argyreia nervosa* (Burn.) Boj. | R |
| *Dichondra repens* Forst | R++ |
| *Quamoclit pennatta* Bojer | S+ |
| *Quamoclit coccinea* (L.) Moen. | R |
| *Merremia tuberosa* (L.) Rend. | R |
| *Stylisma humistrata* (Walt.) Champ. | R |
| Family POLEMONIACEAE | |
| *Cobaea scandens* Cav. | R |
| *Collomia biflora* Brand. | R |
| *Gilia capitata* Sims | R |
| *Gilia tricolor* Benth. | R |
| *Ipomopsis rubra* (L.) Wher. | R |
| *Phlox cuspidata* L. | R |
| *Phlox divaricata* L. | R |
| *Phlox drummondii* Hook "Twinkle Star" | R |
| *Phlox paniculata* L. | R |
| *Polemonium caeruleum* L. | R |
| Family HYDROPHYLLACEAE | |
| *Nemophila menziessii* Hook & Arn. | R |
| *Phacelia tanacetifolia* Benth. | R |
| Family SOLANACEAE | |
| *Atropa belladona* L. | R |
| *Browallia speciosa* Hook. | R |

TABLE 4-continued

Response of various plant species to *Phomopsis convolvulus* under controlled environment conditions.

| SPECIES TESTED | DISEASE REACTION[1] |
|---|---|
| *Capsicum annuun* L. "Green Boy" | R |
| *Capsicum frutescens* L. "Sweet banana" | R |
| *Datura fantuosa* L. "Angels trumpet mixed" | R |
| *Hyosciamus niger* L. | R |
| *Lycopersicum esculentum* Mill. "Campbell 1327", "Better boy" | R |
| *Nicandra physaloides* (L.) Gae. | R |
| *Nicotiana sylvestris* Speg. & Com. | R |
| *Nicotiana tabacum* L. | R |
| *Nierembergia caerula* (M.) Millan | R |
| *Petunia hybrida* Vilm. | R |
| *Petunia parviflora* Juss. | R |
| *Physalis alkekengii* L. | R |
| *Physalis pubescens* L. | R |
| *Physalis ixocarpa* Brot. | R |
| *Physalis pubescens* L. | R |
| *Salpiglossis sinuata* Ruiz & Pavon "F-2 Bolero" | R |
| *Schizanthus pinnatus* Ruiz & Pavon | R |
| *Solanum capsicastrum* Link | R |
| *Solanum dulcamara* L. | R |
| *Solanum melongena* L. "Black beauty" | R |
| *Solanum nigrum* L. | R |
| *Solanum pseudocapsicum* L. | R |
| *Solanum tuberosum* L. "Explorer" | R |
| Family CHENOPODIACEAE | |
| *Beta vulgaris* L. "Red ace" | S+ |
| *Beta vulgaris* L. "Long red mammoth" | R |
| *Beta vulgaris* L. var. rapa "Klein wanzleben" | R |
| Family CHICORACEAE | |
| *Lactuca sativa* L. "Ithaca" | R |
| Family ASTERACEAE | |
| *Carthamus tinctorius* L. "S-296" | S+ |
| *Helianthus annus* L. "Pederovik" | R |
| Family BRASSICACEAE | |
| *Brassica oleracea* L. "Titanic" | R |
| *Brassica oleracea* L. "Snow crown" | R |
| *Raphanus sativum* L. "Champion" | R |
| Family CUCURBITACEAE | |
| *Cucumis melo* L. "Delicious" | R |
| *Cucumis sativum* L. "Slice master" | R |
| *Cucurbita pepo* L. "Jack-O-Lantern" | R |
| Family POACEAE | |
| *Avena sativa* L. | R |
| *Dactylis glomerata* L. "Pennlate" | R+ |
| *Hordeum vulgare* L. "Leger", "Birka" | R+ |
| *Phleum pratense* L. "Timfor" | R+ |
| *Secale cereale* L. "Kustro" | R+ |
| *Sorghum bicolor* (L.) Moench | R |
| *Triticum aestivum* L. "Casavant" | R |
| *Triticum vulgare* L. "Lennox" | R+ |
| *Triticum x Secale* "Experiment.line" | R |

TABLE 4-continued

Response of various plant species to *Phomopsis convolvulus* under controlled environment conditions.

| SPECIES TESTED | DISEASE REACTION[1] |
|---|---|
| *Zea mays* L. "Platinum lady", "Hybrid sucratif" | $R^+$ |
| Family LILIACEAE | |
| *Allium sativum* L. "Titan" | R |
| Family FABACEAE | |
| *Arachis hypogea* L. "Early prolific" | $R^{++}$ |
| *Glycine max* (L.) Merr. "Mapple arrow" | R |
| *Lathyrus odoratus* L. "Super mixture" | R |
| *Lupinus luteus* L. "Minarette" | R |
| Phaseolus lunatus L. "Henderson's bush" | R |
| *Phaseolus coccineus* L. "Scarlet runner" | R |
| *Phaseolus vulgaris* L. "Contender" | R |
| *Pisum sativum* L. "Alaska" | R |
| *Lotus corniculatus* L. "Mirabel" | R |
| *Medicago sativa* L. "Saranac", "Iroquois" | R |
| *Trifolium hybridum* L. "74" | R |
| *Trifolium pratense L.* "Renova" | R |
| *Trifolium repens* L. "Commercial" | R |
| Family POLYGONACEAE | |
| *Fagopyrum esculentum* Gaertn. | R |
| Family ROSACEAE | |
| *Fragaria virginiana* L.[2] "Rugens race vallo" | R |
| Family APIACEAE | |
| *Apium graveolens* L. "Utah giant" | R |
| *Daucus carotta* L. "Imperator" | R |
| Family VITACEAE | |
| *Vitis vinifera* L.[3] "Riesling" | R |

[1]S = susceptible; $S^+$ = limited, localized necrosis; R = resistant; $R^+$ = resistant, but pycnidia formed on incubated, excised senescent leaves; $R^{++}$ = resistant with minor flecking, no pycnidis (hypersensitive)
[2]Only 5 plants inoculated.
[3]Only 2 plants inoculated (5 and 6 leaves each plant).

We claim:

1. A biologically pure culture of the microorganism *Phomopsis convolvulus* IMI 312959.

* * * * *